United States Patent [19]
Faraj

[11] Patent Number: 5,977,009
[45] Date of Patent: Nov. 2, 1999

[54] CATALYST COMPOSITIONS DERIVED FROM TITANIUM-CONTAINING MOLECULE SIEVES

[75] Inventor: Mahmoud K. Faraj, Newtown Square, Pa.

[73] Assignee: Arco Chemical Technology, LP, Greenville, Del.

[21] Appl. No.: 08/831,208

[22] Filed: Apr. 2, 1997

[51] Int. Cl.[6] .............................. B01J 21/06; C01B 39/26
[52] U.S. Cl. ................... 502/64; 502/73; 502/85; 502/215; 502/242; 423/326; 423/713; 423/DIG. 22; 423/DIG. 27; 423/DIG. 29; 423/DIG. 33
[58] Field of Search .................... 502/64, 73, 85, 502/242, 215; 423/713, 714, 715, 326, DIG. 22, DIG. 27, DIG. 29, DIG. 33

[56] References Cited

U.S. PATENT DOCUMENTS

| | | | |
|---|---|---|---|
| 4,410,501 | 10/1983 | Taramasso et al. | 423/326 |
| 4,558,026 | 12/1985 | Bill | 502/159 |
| 4,576,805 | 3/1986 | Chang et al. | 423/277 |
| 4,623,526 | 11/1986 | Sheen . | |
| 4,666,692 | 5/1987 | Taramasso et al. | 423/326 |
| 4,824,976 | 4/1989 | Clerici et al. | 549/531 |
| 4,833,260 | 5/1989 | Neri et al. | 549/531 |
| 4,891,463 | 1/1990 | Chu . | |
| 4,892,720 | 1/1990 | Skeels et al. | 502/85 |
| 4,912,073 | 3/1990 | Chu | 502/85 |
| 5,156,829 | 10/1992 | McCullen et al. | 502/242 |
| 5,374,747 | 12/1994 | Saxton et al. | 549/531 |
| 5,389,358 | 2/1995 | Wu et al. | 723/718 |
| 5,453,511 | 9/1995 | Saxton | 546/191 |
| 5,512,267 | 4/1996 | Davis et al. | 423/706 |

FOREIGN PATENT DOCUMENTS

| | | |
|---|---|---|
| 4425672 | 1/1996 | Germany . |
| 58-159430 | 9/1983 | Japan . |
| 4352771 | 12/1992 | Japan . |
| H8269029 | 10/1996 | Japan . |

OTHER PUBLICATIONS

Millini et al., *Gazzetta Chimica Italiana*, 126, 133–140 (1996) No Month.
Kim et al., *Catalysis Letters* 22, 259–270 (1993) No Month.
Kraushaar–Czarnetzki, et. al., *Catalysis Letters* 2 43–48 (1989) No Month.
Dartt et al., *Applied Catalysis A: General* 143, 53–73 (1996) No Month.
Ferrini et al., "Modified Zealites for Oxidation Reactors", in *New Developments in Selective Oxidation*, pp. 53–60 (1990) (No Month).
Kraushaar et al., *Catalysis Letters* 1, 81–84 (1988) No Month.
Rigutto et al., "Titanium–Containing Large Pore Molecular Sieves . . . ", in *Zeolites & Related Micropernons Materials State of the Art 1994.* vol. 84, 2245–2252 (1994) No Month.
Dann et al., *Inorg. Chem.* 35 (3), 555–558 (1996) No Month.
Miletech, *Monatsheftefur Chemie* 126, 417–430 (1995) No Month.
Sulikowski, *Heterogeneous Chemistry Reviews* 3 203–268 (1996) No Month.

*Primary Examiner*—Mark L. Bell
*Assistant Examiner*—David Sample
*Attorney, Agent, or Firm*—William C. Long

[57] ABSTRACT

Useful catalyst compositions are produced by treating substituted molecular sieves with reactive titanium compounds such as titanium tetrahalides, preferably in the vapor phase at elevated temperatures. The molecular sieve starting materials contain tellurium, boron or germanium oxides in addition to silicon and titanium oxides. Olefins are efficiently transformed to epoxides using these catalyst compositions and an oxidizing agent such as hydrogen peroxide or an organic hydroperoxide.

9 Claims, No Drawings

CATALYST COMPOSITIONS DERIVED FROM TITANIUM-CONTAINING MOLECULE SIEVES

FIELD OF THE INVENTION

This invention pertains to catalyst compositions produced by modifying a molecular sieve isomorphously substituted with Ti and at least one other element selected from Te, Ge and B. The molecular sieves are contacted with reactive titanium compounds such as titanium halide to form the catalyst compositions, which are selective and highly active catalysts for olefin epoxidation.

BACKGROUND OF THE INVENTION

The isomorphous substitution of various elements into the framework of zeolites has received considerable attention in recent years, as such substitution offers interesting opportunities for preparing materials with novel catalytic properties. One such material is titanium silicalite-1 (generally known as TS-1), which is a titanosilicate having an MFI-type structure. Titanium silicalite has been found to be particularly useful in oxidation reactions involving hydrogen peroxide, such as the epoxidation of olefins to yield epoxides. See, for example, U.S. Pat. No. 4,833,260.

However, it has proven to be exceedingly difficult to prepare TS-1 containing a relatively high concentration of Ti atoms in its framework structure. The research group which first prepared TS-1 has reported in numerous publications that it is not possible to incorporate more than 2.5 mole % $TiO_2$ into the TS-1 framework. That is, calcined TS-1 has the molar composition $xTiO_2 \cdot (1-x)SiO_2$, with x ranging from close to 0 to a maximum of 0.025. When a large amount of titanium reagent is utilized in the typical hydrothermal direct synthesis method used to prepare TS-1, the precipitation of extra framework phases (e.g., $TiO_2$ anatase and/or an amorphous titania phase) is observed. See, for example, Millini et al., *Gazzetta Chemica Italiana* 126, 133–140 (1996).

However, other workers have claimed that TS-1 materials containing greater than 2.5 mole % framework titanium may be produced by varying the type of silicon and/or titanium reagent used in the hydrothermal procedure to provide a better match between the hydrolysis rates of these reagents. See, for example, Thangaraj et al., *J. Catalysis* 130, 1 (1991) and Tuel et al., *Appl. Catal.* 110, 137 (1994). Such claims have stimulated an on-going debate over the amount of framework titanium actually present in such "titanium-rich" silicalites and the existence of different titanium sites.

Our investigations of the catalytic performance of the "titanium-rich" silicalites described in the literature have found that certain of these substances (contrary to the predictions of prior art investigators) are capable of providing high epoxide selectivity. See U.S. Pat. No. 5,262,550. However, we have also found that the activity of such materials does not linearly increase as the total titanium content is increased beyond 2.5 mole % $TiO_2$. This suggests that, regardless of whether all the additional titanium atoms being introduced actually are within the lattice framework of the zeolite, not all the titanium sites are equally active catalytically. Generally speaking, it will be desirable to use a catalyst having the maximum activity possible (as measured by moles of reactants converted per unit of time for a given weight of catalyst). The presence of titanium atoms which are unavailable to function as active catalyst sites or which convert the reactants at a slower rate than other sites results in a titanium silicalite having less than optimum catalytic activity.

Secondary routes for preparing TS-1 titanium silicalite have also been investigated, wherein a pre-synthesized MFI-type zeolite is treated with a volatile or water-soluble titanium compound. For example, an acid-leached ZSM-5 may be reacted with gaseous titanium tetrachloride (see Kraushaar et al., *Catal. Lett.* 1, 81 (1988), Kraushaar-Czarnetzki et al., *Catal. Lett.* 2, 43 (1989), and Huybrechts et al., *Catal. Lett.* 8, 237 (1991)). Unfortunately, the concentration of titanium incorporated by known secondary synthesis materials is even lower than that obtained by hydrothermal procedures. Attempts to increase the amount of titanium using secondary synthesis techniques similarly leads to the production of extra framework titanium species. Moreover, according to the previously mentioned Huybrechts et al. article, materials made by such methods are very poor olefin epoxidation catalysts when compared to titanium silicalites prepared by direct synthesis.

SUMMARY OF THE INVENTION

I have now found that highly active catalyst compositions may be easily prepared by contacting a reactive titanium compound with a molecular sieve comprised of oxides of Si, Ti and at least one additional element selected from the group consisting of Te, B and Ge. These compositions are particularly useful for converting olefins to epoxides using active oxygen species such as hydrogen peroxide or organic hydroperoxides.

DETAILED DESCRIPTION OF THE INVENTION

The catalyst compositions of this invention are prepared using molecular sieves. While the framework structure of the molecular sieve is not critical, where the catalyst composition is to be used as in olefin epoxidation it is desirable to employ a molecular sieve characterized by an MFI, MEL, BEA, MTW, ZSM-48 or MCM-41 topology. An MFI framework structure is most preferred where the oxidant is hydrogen peroxide and the olefin is relatively small (e.g., propylene). The framework structure of suitable molecular sieves is comprised of oxides of Si, Ti and at least one additional element selected from the group consisting of Te, B and Ge. For example, the molecular sieve may contain Si, Ti and B, or Si, Ti and Te, or Si, Ti and Ge. Mixtures of B and Te, Te and Ge, B and Ge, or B, Te and Ge may, of course, also be present together with the required Si and Ti atoms.

Suitable molecular sieves may be described as synthetic materials containing silicon oxide, titanium oxide and either tellurium oxide, boron oxide, germanium oxide or combinations thereof and having crystalline, porous, structures of zeolitic character which in preferred embodiments of the invention are similar to that of ZSM-5, ZSM-11, beta, ZSM-12, ZSM-48 or MCM-41 zeolite. In a calcined and anhydrous state, such molecular sieves will generally correspond to the empirical formula: $SiO_2 : aTiO_2 : bMO_y$, wherein "a" is typically from 0.005 to 0.10, "b" is typically from 0.005 to 0.2, M is Te, B, Ge or a combination thereof, and "y" is a number effective to satisfy the valency of M. Expressed as a percentage by weight of the calcined and anhydrous material, in preferred embodiments of the invention the Ti content ranges from about 0.1 to 4.5% and the M content ranges from about 0.05 to 5%. Generally speaking, the epoxidation activity of the catalyst composition obtained from the molecular sieve will tend to increase as the titanium content and M content are increased within these ranges.

Without wishing to be bound by theory, it is believed based on analytical characterization of these molecular sieve starting materials that titanium and M atoms are substituted for silicon atoms in a zeolite type framework.

Certain of the molecular sieve starting materials suitable for purposes of this invention are well-known in the art and may be synthesized by any conventional method. For example, molecular sieves of MFI topology containing silicon oxides, titanium oxides, and boron oxides are described in Kapoor et al., *Catalysis Letters* 43, 127–131 (1997) and Trong On et al., *J. Chem. Soc. Faraday Trans.* 92 (6), 1031–1038 (1996).

Other suitable molecular sieves may be prepared by a process wherein under hydrothermal conditions a derivative of silicon, a derivative of titanium, a derivative of M (wherein M=Te, B, Ge or mixture thereof), and a nitrogenous organic base are reacted. The $SiO_2/MO_y$ molar ratio of the reactants is desirably greater than 50 but less than 600 (more preferably, less than 200). Operation within the range of from 80 to 140 is particularly advantageous. The $SiO_2/TiO_2$ molar ratio of the reactants is desirably greater than 5, but less than 450, with the range of from 10 to 40 being especially advantageous. The $H_2O/SiO_2$ molar ratio of the reactants is desirably in the range of from 10 to 100, preferably within the range of 25 to 50. Although an alkali metal or alkaline earth metal compound such as an alkali metal hydroxide may also be present, generally it will be desirably to maintain the $X/SiO_2$ molar ratio (where X is the alkali metal or alkaline earth metal) lower than 0.1, preferably lower than 0.01, or equal to 0. Preferably, all of the basic ions (e.g., hydroxide) needed in the reactor mixture are supplied by the nitrogenous organic base. Similarly, although oxides of other substances such as aluminum oxides and the like could be introduced into the molecular sieve, the amounts of such other oxides in preferred embodiments of the invention are kept low relative to the amounts of $TiO_2$ and $MO_2$ which are present. In preferred embodiments, the molecular sieve is essentially aluminum free (i.e., less than 500 ppm Al). The molecular sieve may, for example, consist essentially of silicon oxides, titanium oxides, and either tellurium oxides, boron oxides, germanium oxides or a combination thereof. The reagents used should be substantially free of aluminum, although the trace quantities of Al normally present in such materials will ordinarily not be detrimental to catalyst performance to a significant degree.

Although the silicon derivative may be any substance capable of functioning as a source of $SiO_2$ in a hydrothermal synthesis, such as, for example, silica gel or silica sol, the silicon derivative preferably is a tetraalkyl orthosilicate such as tetramethyl orthosilicate or tetraethyl orthosilicate. Similarly, while the titanium derivative may be any substance capable of functioning as a source of $TiO_2$ in a hydrothermal synthesis, such as, for example, a titanium salt (e.g., titanium halide), in preferred embodiments of the invention the titanium derivative is a tetraalkyltitanate where the alkyl groups are $C_1$–$C_6$ alkyl groups such as methyl, ethyl, n-propyl, n-butyl, sec-butyl, iso-butyl, tert-butyl and the like. Tetra n-butyl orthotitanate is a particularly preferred titanium derivative. Likewise, the derivative of Te, B, or Ge may be any substance capable of functioning as a source of tellurium oxide, boron oxide or germanium oxide in a hydrothermal synthesis. While salts such as halides and hydroxides could be utilized, it is preferred to use tellurium, boron or germanium alkoxides where the alkoxide groups are preferably $C_1$–$C_6$ alkoxide groups such as ethoxide, propoxide and the like. Co-precipitate or co-gels of Si, Ti and M, Si and Ti, Si and M, Ti and M, or Si and M can also be used as starting materials.

The nitrogenous organic base is preferably an alkyl ammonium hydroxide, preferably a quaternary alkyl ammonium hydroxide. The nitrogenous organic base may alternatively comprise a mixture of an alkyl ammonium halide (e.g., tetrapropyl ammonium bromide) and an organic amine (e.g., triethylamine, ethylenediamine). The $NOB/SiO_2$ molar ratio (where NOB=nitrogenous organic base) of the reactants is desirably maintained in the range of from 0.1 to 1, preferably from 0.2 to 0.5. The morphology of the molecular sieve may be controlled as desired by varying the structure of the nitrogenous organic base employed. Without wishing to be bound by theory, it is believed that the cation portion of the nitrogenous organic base functions as a template or structure directing agent. The size and shape of the cation appears to influence the hydrothermal crystallization process such that the framework of the resulting molecular sieve assumes either an MFI (ZSM-5), MEL (ZSM-11), BEA (beta), MTW (ZSM-12), MCM-41, ZSM-48, or other desired topology. For example, the use of tetrapropyl ammonium hydroxide leads to formation of an MFI framework. Where the cation is tetrabutyl ammonium or dialkyl 3,5-dimethyl piperidinium (see WO 96/34827), an MEL structure is produced. To obtain a BEA framework structure, 4,4'-trimethylene bis (N-benzyl N-methyl piperidenium) dihydroxide (see U.S. Pat. No. 5,453,511) may be employed. If a titanium-containing molecular sieve having a ZSM-48 topology is desired, the nitrogenous organic base may comprise a trimethylpropylammonium cation (see Tuel et al., *Zeolites* 15, 164–170 (1995)) or hexamethonium cation (see Reddy et al., *Catal. Lett.* 23, 169–173 (1994)). Where the titanium-containing molecular sieve has an MCM-41 framework structure, a cation containing a relatively long chain hydrocarbon chain (e.g., $C_{10}$–$C_{18}$) such as cetyltrimethylammonium may be utilized (see EP 655,278). A molecular sieve having an MTW (ZSM-12) framework structure may be prepared using hexamethylene bis (diethylmethylammonium) cation (see Tuel, *Zeolites* 15, 236–242 (1995)).

The above-described reactants are combined with each other, either sequentially or simultaneously, and the resulting mixture (which may be in the form of a gel) heated in the presence of water at a temperature of from 100° C. to 200° C., preferably from 140° C. to 185° C., at a basic pH (e.g., within the range of 8 to 14) for a time period effective to cause crystals of the desired as-synthesized molecular sieve to form (generally from 1 hour to 10 days, with hydrothermal reaction times of from 6 hours to 3 days typically being preferred). The crystals may be allowed to nucleate spontaneously from the reaction mixture. Alternatively, the reaction mixture may be seeded with crystals of the desired molecular sieve to direct and accelerate the crystallization. The hydrothermal crystallization is usually conducted under pressure and usually in an autoclave so that the reaction mixture is subject to autogenous pressure. The reaction mixture can be stirred or otherwise agitated during crystallization. If so desired, the alcohols(s) derived from the starting reagents may be fully or partially removed by distillation, evaporation or the like prior to hydrothermal treatment. Once crystallization has proceeded to the desired extent, the crystals of as-synthesized molecular sieve may be isolated by any suitable conventional method from the liquid components of the reaction mixture such as filtration, centrifugation, decantation or the like. The as-synthesized molecular sieve will generally contain residual nitrogenous organic base, which may be removed by calcination (preferably, in the presence of oxygen) at an elevated temperature (typically, 300° C. to 800° C.) for a period of 0.5 to 24 hours. It is desirable to calcine the molecular sieve prior to contacting with the reactive titanium compound. Prior to calcination, the as-synthesized molecular sieve may be washed with a suitable solvent such as water or alcohol and then dried at relatively low temperatures (e.g., 90° C. to 150° C. at atmospheric or subatmospheric pressures).

It is neither necessary nor desirable to treat the molecular sieve with acid or the like prior to contacting with the reacting titanium compound.

Reactive titanium compounds suitable for the purposes of the present invention generally include those compounds conforming to the formula $TiR_4$ wherein the R groups are the same or different and are preferably radicals selected from the group consisting of alkoxy, aryloxy, dihydrocarbon substituted amino and halide. Titanium compounds in lower oxidation states may also be used. The use of titanium halides is particularly advantageous; examples of such compounds include, but are not limited to, titanium tetrachloride, titanium tetrafluoride, titanium trichloride, titanium trifluoride, titanium tetrabromide, titanium tetraiodide, dibromo titanium dichloride, and the like. Titanium tetrachloride is most preferred for use in the present invention. Examples of other reactive titanium compounds which may be used include titanium butoxide, titanium diisopropoxide bis(2,4-pentanedionate), titanium ethoxide, titanium isopropoxide, titanium propoxide, titanium cresylate, titanium 2-ethyl hexoxide, titanium isobutoxide, titanium methoxide, tetrakisdipentylaminotitanium, tetrakismethylpropylaminotitanium and the like. Mixtures of reactive titanium compounds may be utilized if so desired. "Reactive" in this context means that the titanium is substituted with at least one group capable of being displaced by a nucleophile such as a hydroxyl group or the like.

The conditions under which contact between the reactive titanium compound and the aforedescribed molecular sieve can be accomplished are subject to considerable variation. However, in order to obtain products possessing a high order of activity and reproducible character, it is normally desirable to exclude water, i.e., to contact the molecular sieve and reactive titanium compound under anhydrous conditions. If either reactant contains molecular water in any form, it should be dried before use.

The molecular sieve is maintained in intimate contact with the reactive titanium compound for a period of time sufficient to effect the desired modification of the molecular sieve. It is believed, although there is no intent to be bound by this explanation, that the titanium present in the reactive titanium compound combines in some way with the surface of the molecular sieve in a manner such that it becomes chemically bonded to at least one oxygen atom in the molecular sieve surface. For example, silanol or M—OH groups may react with the reactive titanium compound. "Surface" in this context can include framework positions within the lattice of the molecular sieve. It has been observed that the M (B, Ge, Te) content of the molecular sieve is typically lower after contacting the molecular sieve with the reactive titanium compound, suggesting that at least some of the M atoms are being displaced in some manner by titanium atoms derived from the reactive titanium compound. The catalyst composition which is obtained is still substantially or entirely crystalline and is zeolitic in character, but has a Ti content which is elevated relative to the composition of the molecular sieve starting material. Typically the total Ti in the catalyst composition will be increased at least 10% on a weight basis. Generally speaking, it will be desirable to achieve Ti levels of from 3 to 8 weight % (corresponding approximately to a range of 4 to 10 mole %), with levels of from 3.5 to 5 weight % (4.5 to 6.5 mole %) being favored when the catalyst composition is to be used in olefin epoxidation.

A particularly desirable way of performing the required contacting step is to expose the molecular sieve to sufficient quantities of vapors of the reactive titanium compound at an elevated temperature. Generally speaking, temperatures higher than room temperature will be satisfactory. The optimum temperature will vary depending upon the reactive titanium compound selected for use. Where a titanium halide is used, for example, temperatures of from 200° C. to 500° C. will typically be preferred. Assuming provision is made for intimate contact between the molecular sieve and the reactive titanium compound, the time required to accomplish the desired modification of the molecular sieve generally varies from a few minutes to periods of days. Lower contact temperatures will generally require somewhat longer reaction times. The vapors of the reactive titanium compound can be supplied under their own vapor pressure, using a partial vacuum if necessary, or with the aid of a gaseous carrier, preferably one that is dry and inert such as helium or nitrogen. This vapor phase treatment can be accomplished in any suitable manner such as by circulating the vapors through the solid molecular sieve in a fixed or moving bed reactor.

Alternatively, the modification of the molecular sieve by the reactive titanium compound may also be accomplished by contacting a solution of the reactive titanium compound with the molecular sieve. The solvent used for such purpose is preferably anhydrous and non-reactive (hydrocarbons such as alkanes and aromatic compounds, for example, are suitable solvents). Suitable contact temperatures and times are similar to those discussed above for the vapor phase method.

Following treatment with the reactive titanium compound, the resulting catalyst composition may be further modified if so desired. For example, the catalyst composition may be calcined by heating at an elevated temperature (e.g., 400° C. to 800° C.) in the presence of oxygen or the like. The catalyst composition may also be contacted with water. Said contacting may be conveniently be accomplished by placing the catalyst composition into a fixed bed apparatus and passing steam or an inert gas saturated with water vapor through the bed (temperatures of from 100° C. to 600° C. for 0.5 to 12 hours are typically sufficient for such purpose). Another treatment method is to react the catalyst composition with a silylating agent or other neutralizing agent in a manner analogous to the procedures described in U.S. Pat. No. 4,824,976. In yet another embodiment, the catalyst composition is washed with a suitable solvent to remove impurities or the like. The catalyst composition may be advantageously subjected to more than one of the aforedescribed modifications if so desired. For example, the catalyst composition may be sequentially calcined, contacted with water, and silylated.

The catalyst compositions of this invention have application as molecular sieves for separating compounds based on molecular size or shape and as catalysts in the following reactions: cracking, selectoforming, hydrogenation, dehydrogenation, oligomerization, alkylation, isomerization, dehydration, hydroxylation, and the like. Molecular sieves modified with reactive titanium compounds in accordance with this invention are particularly useful for catalyzing the same types of oxidation reactions as known titanium zeolites such as TS-1, TS-2, Ti-ZSM-11, Ti beta, and like. Examples of such reactions include olefin epoxidation, alkane oxidation, phenol hydroxylation, ammoximation of ketones and the like. Catalyst compositions may be prepared in accordance with this invention having titanium levels significantly in excess of those readily obtainable by conventional hydrothermal or direct synthesis methods. Moreover, the catalytic activity of the composition is in many cases directly proportional to the titanium content. This result was surprising, since the relationship between titanium content and activity for the "high titanium" zeolites described in the prior art becomes increasingly non-linear as the amount of titanium is increased, suggesting that at least some of the additional titanium is being incorporated in a manner not able to function as a catalytic site. The catalyst compositions of the present invention, however, may be considered to be more efficient catalysts since substantially all of the titanium present appears to be in active form.

The compositions of this invention are especially useful for catalyzing the reaction of olefins with an active oxygen species such as hydrogen peroxide or an organic hydroperoxide to form epoxides. The amount of catalyst composition employed to epoxidize an olefin is not critical, but should be sufficient so as to substantially accomplish the desired reaction in a practicably short period of time. The optimum quantity of catalyst composition will depend upon a number of factors including reaction temperature, olefin reactivity and concentration, active oxygen species concentration, type and concentration of organic solvent as well as catalyst activity. Typically, however, in a batch type epoxidation, the amount of catalyst composition will be from 0.001 to 10 grams per mole of olefin. In a fixed bed system, the optimum quantity of catalyst composition will be influenced by the flow of reactants through the fixed bed (typically, from about 1 to 100 moles per kilogram of catalyst per hour). The concentration of titanium in the total epoxidation reaction mixture will generally be from about 10 to 10,000 ppm.

The catalyst composition may be utilized in powder, pellet, microspheric, monolithic, extruded, or any other suitable physical form. The use of a binder (co-gel) or support in combination with the reactive titanium compound-modified molecular sieve may be advantageous. Supported or bound catalyst may be prepared by the methods known in the art to be effective for zeolite catalysts in general.

The olefin substrate epoxidized in the process of this invention may be any organic compound having at least one ethylenically unsaturated functional group (i.e., a carbon-carbon double bond) and may be a cyclic, branched or straight chain olefin. The olefin may contain aryl groups. The use of light (low-boiling) $C_2$–$C_{10}$ mono-olefins such as ethylene, propylene, 1-butene, 2-butene, 1-pentene, cyclohexene, and the like is especially preferred.

The oxidizing agent employed in the process of this invention may be hydrogen peroxide ($H_2O_2$), including compounds which under the epoxidation reaction conditions are capable of generating or liberating hydrogen peroxide. Hydrogen peroxide obtained by operation of any known process may be utilized, including air oxidation of anthraquinone, methyl benzyl alcohol, isopropyl alcohol, and the like. The hydrogen peroxide may be formed in situ, if so desired. For example, the catalyst composition could be further modified by incorporation of a Group VIII transition metal such as Pd or Pt. Oxygen and hydrogen are then fed to the epoxidation reactor containing the transition metal-modified catalyst.

The Group VIII transition metal(s) may be incorporated into the catalyst composition (or, alternatively, the molecular sieve prior to treatment with the reactive titanium compound) using any suitable method such as, for example, impregnation (preferred), precipitation, blending, or the like. A solution of a Group VIII transition metal in a suitable solvent may be combined with the catalyst composition using an incipient wetness technique, for instance, and the resulting metal-impregnated catalyst composition dried and calcined if desired. Full or partial reduction of the transition metal may be performed prior to use of the catalyst composition as an oxidation catalyst. The amount of Group VIII transition metal supported on the catalyst composition is typically 0.01 to 10 percent by weight, preferably 0.05 to 5 percent by weight calculated as metal relative to the total weight of the catalyst. The methods described in Japanese Kokai Nos. 4-352771 and H8-269029 and in DE 4,425,672 for the preparation and use of transition metal-modified titanium zeolites may be readily adapted for use with the catalyst compositions of this invention.

The amount of hydrogen peroxide relative to the amount of olefin is not critical, but most suitably the molar ratio of $H_2O_2$:olefin is from 100:1 to 1:100. When the olefin contains one ethylenically unsaturated group, the olefin substrate to hydrogen peroxide molar ratio is typically in the range of from 1:10 to 10:1. One equivalent of hydrogen peroxide is theoretically required to oxidize one equivalent of a mono-unsaturated olefin substrate, but it may be desirable to employ an excess of one reactant to optimize selectivity to the epoxide.

When the molecular sieve has relatively large pores, organic hydroperoxides such as ethyl benzene hydroperoxide, t-butyl hydroperoxide and the like may replace hydrogen peroxide as the oxidizing agent. Suitable reaction conditions will generally be similar to those previously described herein where the oxidizing agent is hydrogen peroxide.

If desired, a solvent may additionally be present during the epoxidation process of this invention in order to dissolve the reactants other than the catalyst composition, to provide better temperature control, or to favorably influence the epoxidation rates and selectivities. The solvent, if present, may comprise from 1 to 99 weight percent of the total epoxidation reaction mixture and is preferably selected such that it is a liquid at the epoxidation reaction temperature. Organic compounds having boiling points at atmospheric pressure of from about 25° C. to 300° C. are generally preferred for use. Excess olefin may serve as a solvent or diluent. Illustrative examples of other suitable solvents include, but are not limited to, ketones, ethers, aliphatic and aromatic hydrocarbons, halogenated hydrocarbons, and alcohols. Water may also be present in the epoxidation reaction mixture without significant adverse effect.

A basic, neutral or acidic salt containing alkali metal, alkaline earth metal or ammonium cations such as ammonium hydroxide, ammonium acetate, sodium chloride, sodium pyrophosphate, ammonium nitrate, sodium sulfate, potassium hydroxide and the like may be present at low concentrations in order to improve selectivity to the epoxide.

The reaction temperature is not critical, but should be sufficient to accomplish substantial conversion of the olefin to epoxide within a reasonably short period of time. It is generally advantageous to carry out the reaction to achieve as high a conversion of oxidizing agent as possible, preferably at least 50%, more preferably at least 90% most preferably at least 95%, consistent with reasonable selectivities. The optimum reaction temperature will be influenced by catalyst activity, olefin reactivity, reactant concentration, and type of solvent employed, among of other factors, but typically will be in a range of from about 0° C. to 150° C. (more preferably, from about 25° C. to 120° C.). Reaction or residence times of from about 1 minute to 48 hours (more desirably, from about 10 minutes to 8 hours) will typically be appropriate, depending upon the above-identified variables. Although subatmospheric pressures can be employed, the reaction is preferably (especially when the boiling point of the olefin is below the epoxidation reaction temperature) performed at atmospheric pressure or at elevated pressure (typically, between 1 and 100 atmospheres). Generally, it will be desirable to pressurize the epoxidation vessel sufficiently to maintain the reaction components as a liquid phase mixture. For example, performing the epoxidation at elevated pressure will increase the solubility of gaseous reactants such as propylene in the solvent and oxidizing agent.

The epoxidation process of this invention may be carried out in a batch, continuous, or semi-continuous manner using any appropriate type of reaction vessel or apparatus such as a fixed bed, transport bed, fluidized bed, stirred slurry, or CSTR reactor in a monophase or biphase system. Known methods for conducting metal-catalyzed epoxidations of olefins using an active oxygen oxidizing agent will generally also be suitable for use in this process. Once the epoxidation has been carried out to the desired degree of conversion, the epoxide product may be separated recovered from the reaction mixture using any appropriate technique such as fractional distillation. After separating from the epoxidation reaction mixture by any suitable method such as filtration, the recovered catalyst may be economically reused in subsequent epoxidations. Where the catalyst composition is deployed in the form of a fixed bed, the epoxidation product withdrawn as a stream from the epoxidation zone will be essentially catalyst free with the catalyst being retained within the epoxidation zone. In certain embodiments of the instant process where the epoxide is being produced on a continuous basis, it may be desirable to periodically or constantly regenerate all or a portion of the used catalyst in order to maintain optimum activity and selectivity. Suitable regeneration techniques include, for example, treating the catalyst composition with solvent at an elevated temperature or calcining the catalyst composition.

EXAMPLES

EXAMPLE 1

This example illustrates the preparation of a catalyst composition in accordance with the invention using a molecular sieve comprised of oxides of silicon, titanium, and tellurium and having an MFI framework structure. The molecular sieve is prepared as follows: a solution of 22.50 g tetraethyl orthosilicate, 2.1 g tetra n-butyl orthotitanate and 0.30 g tellurium ethoxide (85 wt. % in ethanol) was mixed for 30 minutes at room temperature. The resulting mixture was added dropwise to 50 g tetrapropyl ammonium hydroxide (1 M or 20 wt. % in water). The mixture was stirred at room temperature for 18 hours, then transferred to a Teflon-lined autoclave. Hydrothermal treatment of the mixture was performed in a 175° C. oven for 24 hours. The crystalline product thereby formed was removed by centrifugation, washed three times with distilled water, vacuum dried at 120° C. for 2 hours, and then calcined in air at 510° C. to yield the molecular sieve. The calcined molecular sieve contained 41 wt. % Si, 2 wt. % Ti, and 0.2 wt. % Te by elemental analysis. The Si/Ti ratio was 35. No anatase or tellurium oxide phase was detected by x-ray diffraction. The XRD pattern was similar to that of TS-1 titanium silicalite.

The calcined molecular sieve (4 g) was loaded in a tubular glass reactor, then heated at 350° C. under a helium flow of 50 cc/minute for 2 hours. Thereafter, 2 g titanium tetrachloride (99.9%) was added through the septum of a three neck flask connected to the tubular reactor. Treatment with the titanium tetrachloride was terminated after 8 hours and the resulting catalyst composition calcined in air for 10 hours at 510° C.

EXAMPLE 2

This example illustrates the preparation of a catalyst composition in accordance with the invention using a molecular sieve comprised of oxides of silicon, titanium and germanium and having an MFI framework structure. The procedure of Example 1 is repeated, except that an equimolar amount of germanium ethoxide is substituted for the tellurium ethoxide.

EXAMPLE 3

This example illustrates the preparation of a catalyst composition in accordance with the invention using a molecular sieve comprised of oxides of silicon, titanium, and boron and having an MFI framework structure. The procedure of Example 1 is repeated, except that an equimolar amount of boron isopropoxide is substituted for the tellurium ethoxide.

EXAMPLES 4–6

These examples demonstrate the advantages of the catalytic compositions of this invention (Examples 5–6) as compared to a conventional TS-1 titanium silicalite prepared by a hydrothermal direct synthesis method (Comparative Example 4). The catalyst compositions used in Examples 5 and 6 were prepared in accordance with the procedures of Examples 1 and 2, respectively. The catalyst composition of Comparative Example 4, which contained 1.5 weight % Ti, was prepared in accordance with the procedures described in Clerici et al., *J. Catalysis* 129, 159–167 (1991). The performance of these materials as propylene epoxidation catalysts was evaluated under the following conditions: 0.1 g catalyst in 40 g of a mixture containing 5.6 wt. % hydrogen peroxide, 10 wt. % water, 84 wt. % methanol, 0.2 wt. % formic acid, 0.3 wt. % acetic acid, and 27 ppm diammonium hydrogen phosphate, 60° C., 30 minutes. The results obtained are summarized in Table I.

TABLE I

| Example No. | Ti, wt % | M, wt % | $H_2O_2$ Conv. % | PO Selectivity, % | K. $hr^{-1}$ |
|---|---|---|---|---|---|
| $4^1$ | 1.5 | — | 58 | 91.5 | 1.84 |
| 5 | 3.4 | $0.02^2$ | 96.5 | 90 | 6.85 |
| 6 | 2.8 | $0.19^3$ | 80.5 | 91 | 3.4 |

[1]comparative
[2]M = Te
[3]M = Ge

The catalyst compositions of Examples 5 and 6 were found to be as selective as the conventional TS-1 titanium silicalite of Comparative Example 4, yet approximately two to three times more active. These results suggest that the additional titanium atoms introduced by way of titanium tetrachloride treatment are essentially fully active and available to function as olefin epoxidation sites.

I claim:

1. A catalyst composition essentially free of Al oxides and useful for the epoxidation of olefins obtained by contacting a reactive titanium compound with a molecular sieve having an MFI framework structure comprised of oxides of Si, Ti and at least one additional element selected from the group consisting of Te, B and Ge, the said molecular sieve having in a calcined anhydrous state the general formula $SiO_2:aTiO_2:bMO_y$, wherein a is 0.005 to 0.10 and b is from 0.005 to 0.2, M is Te, B, Ge or combination thereof, and y is a number effective to satisfy the valency of M.

2. The catalyst composition of claim 1 wherein the reactive titanium compound is a titanium halide.

3. The catalyst composition of claim 1 wherein the additional element is Te.

4. The catalyst composition of claim 1 wherein Ti comprises from 3 to 8 weight percent of the catalyst composition.

5. A method of making a catalyst composition essentially free of Al oxides and useful for the epoxidation of olefins which comprises contacting a reactive titanium compound with a molecular sieve having an MFI framework structure comprised of oxides of Si, Ti and at least one additional element selected from the group consisting of Te, B and Ge, the said molecular sieve having in a calcined anhydrous state, the general formula $SiO_2:aTiO_2:bMO_y$, wherein a is 0.005 to 0.10 and b is from 0.005 to 0.2, M is Te, B, Ge or a combination thereof, and y is a number effective to satisfy the valency of M.

6. The method of claim 5 wherein the reactive compound is a titanium halide.

7. The method of claim 5 wherein said contacting is carried out in the vapor phase.

8. The method of claim 5 wherein said contacting is performed at a temperature of from 250° C. to 450° C.

9. The method of claim 5 comprising the additional step of calcining in the presence of oxygen.

* * * * *